United States Patent [19]

James

[11] Patent Number: 5,601,618
[45] Date of Patent: Feb. 11, 1997

[54] STIMULATION AND HEATING DEVICE

[76] Inventor: Brian C. James, 888 Boulevard of the Arts, #803, Sarasota, Fla. 34236

[21] Appl. No.: 606,585

[22] Filed: Feb. 26, 1996

[51] Int. Cl.$^6$ .................. A61N 1/18; A61F 7/00
[52] U.S. Cl. .................. 607/71; 607/148; 607/149
[58] Field of Search .................. 607/71, 96, 98, 607/112, 149, 148

[56] References Cited

U.S. PATENT DOCUMENTS

| 940,151 | 11/1909 | Heath | 607/96 |
| 5,097,828 | 3/1992 | Deutsch . | |
| 5,336,255 | 8/1994 | Kanare et al. | 607/149 |

*Primary Examiner*—Angela D. Sykes
*Assistant Examiner*—Rosiland Kearney
*Attorney, Agent, or Firm*—Charles J. Prescott

[57] ABSTRACT

A combination soft body tissue stimulator and heating device including a thin, flat, molded flexible plastic pad, one side of which defines a working surface. The molded pad has a plurality or an array of spaced separate conductive areas each having an exposed conductive surface which is generally coplanar with the working surface. When the device is properly installed, each conductive area makes electrical contact with, and receives support from, a separate disposable double-sided flexible adhesive electrode attached to the skin over the soft tissue. The array of electrodes adhesively attached to the skin is generally aligned with the array of conductive areas of the pad so that only the adhesive attachment between the conductive areas and the electrodes is required to hold the device in place against the skin. A resistive heating element is embedded within the pad which is generally coextensive with and electrically isolated from the array of conductive areas on the side thereof away from the working surface. The conductive areas are connectable to a pulsed electrical current and the heating element is connectable to a d.c. battery supply for simultaneous stimulation and heating of any desired soft body tissue area.

3 Claims, 1 Drawing Sheet

STIMULATION AND HEATING DEVICE

BACKGROUND OF THE INVENTION

Scope of Invention

This invention relates generally to therapeutic devices for treating distressed soft body tissue and more particularly to a device for therapeutic electrical stimulation and simultaneously heating of soft body tissue.

Prior Art

Therapeutic electrical stimulation of soft body tissue is well known. These devices which produce transcutaneous electrical nerve stimulation are known as TENS devices and are used to both relieve chronic pain and to produce muscle building stimulation. It is also well known to treat injured and weakened soft body tissue through the use of the topical application of heating atop the body tissue to be treated.

Many devices beginning with the earliest of the resistive wire heating pads are well known in prior art to accomplish the individual function of heating. The more recently developed TENS units are well known for therapeutic electrical stimulation of muscles and soft body tissue. A more complex therapeutic device for providing heating or cooling of the skin and underlying body tissue is disclosed in U.S. Pat. No. 5,097,828 invented by Deutsch. This device includes a handle and a thermally conductive head which utilizes Peltier effect devices for heating or cooling a contact plate within the head. The contact plate may also be connected to a high-voltage source for electrical stimulation.

In U.S. Pat. No. 5,336,255, Kanare et al. have disclosed an electrical stimulation and heating or cooling pack which includes a nonconductive pouch and straps for positioning and holding the pouch against a body part. Flexible conductive patches attached to the pouch are connectable to a remote pulse generator. An electrically conductive adhesive gel pad is also provided for coupling the conductive patch to the body part. By this arrangement, both heating or cooling and electrical stimulation of a body part are provided.

The present invention discloses a very simple device for providing combination electrical stimulation or TENS-type soft body tissue stimulation and the simultaneous heating of the body tissue. The device is hermetically sealed and extremely compact and portable, relying upon low current dry battery power for heating and the utilization of double-sided adhesive conductive electrodes which adhesively attach to the skin area over the soft body tissue for supporting the device against the skin during use.

BRIEF SUMMARY OF THE INVENTION

This invention is directed to a combination soft body tissue stimulator and heating device including a thin, flat, molded flexible plastic pad, one side of which defines a working surface. The molded pad has a plurality or an array of spaced separate conductive areas each having an exposed conductive surface which is generally coplanar with the working surface. When the device is properly installed, each conductive area makes electrical contact with, and receives support from, a separate disposable double-sided flexible adhesive electrode attached to the skin over the soft tissue. The array of electrodes adhesively attached to the skin is generally aligned with the array of conductive areas of the pad so that only the adhesive attachment between the conductive areas and the electrodes is required to hold the device in place against the skin. A resistive heating element is embedded within the pad which is generally coextensive with and electrically isolated from the array of conductive areas on the side thereof away from the working surface. The conductive areas are connectable to a pulsed electrical current and the heating element is connectable to a d.c. battery supply for simultaneous stimulation and heating of any desired soft body tissue area.

It is therefore an object of this invention to provide a portable, compact device for the simultaneous therapeutic electrical stimulation and heating of soft body tissue.

It is another object of this invention to provide a device for therapeutic electrical stimulation and simultaneous heating of soft body tissue which is adhesively connectable to the skin and held in place by double-sided adhesive electrodes only.

It is yet another object of this invention to provide a device for therapeutic electrical stimulation and simultaneous heating of soft body tissue which is hermetically sealed, extremely compact and portable and utilizes independent low levels of voltage electrically isolated one from another for both therapeutic functions.

It is yet another object of this invention to provide a flexible device for the therapeutic electrical stimulation and simultaneous heating of virtually any portion of soft body tissue.

In accordance with these and other objects which will become apparent hereinafter, the instant invention will now be described with reference to the accompanying drawings.

DETAILED DESCRIPTION OF THE INVENTION

Figure 1:
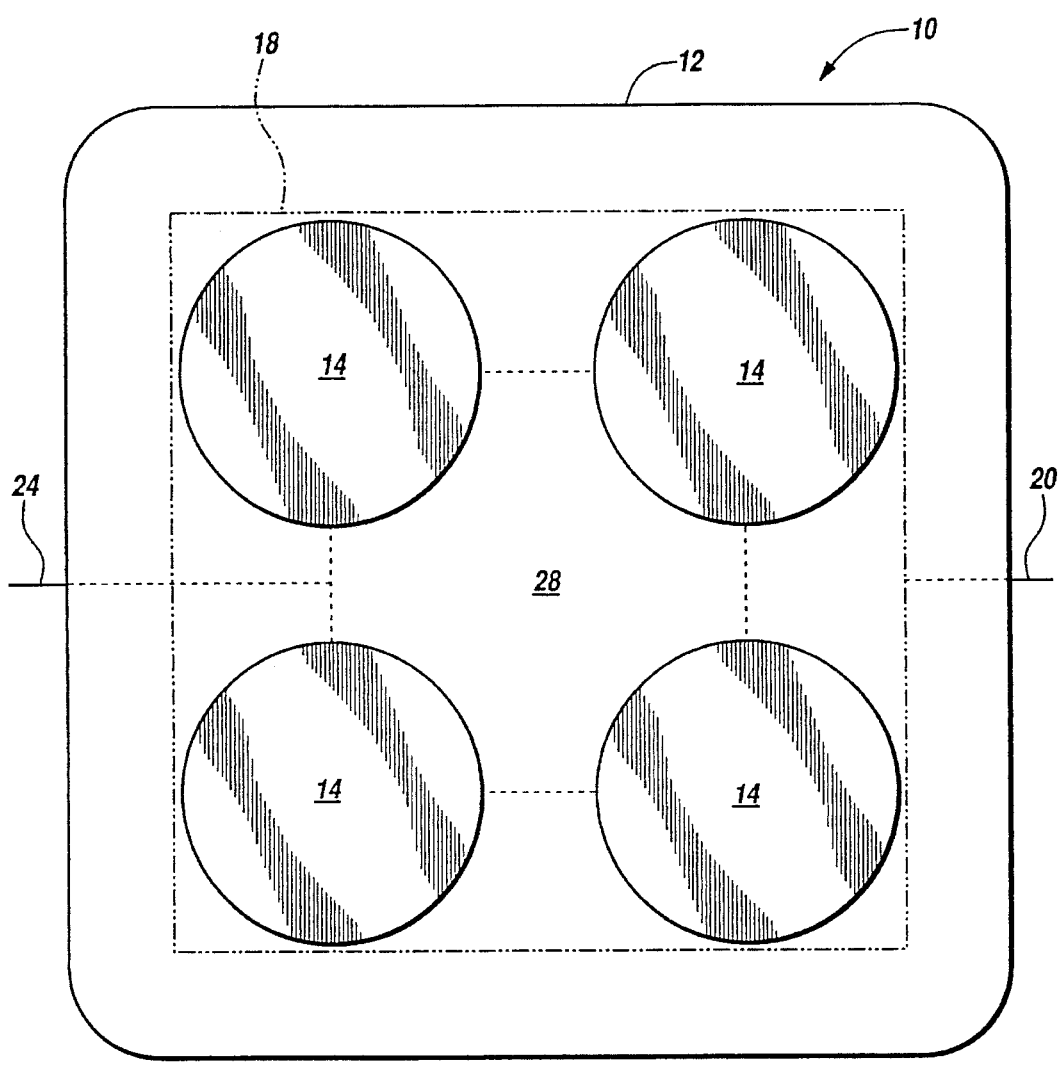
FIG. 1 is a plan view of the working surface of the device.

Referring now to the drawings, the preferred embodiment of the invention shown generally at numeral 10 and includes a thin, generally rectangularly shaped molded flexible plastic pad 12 one side of which defines a flat working surface 28. The molded pad 12 includes an array of evenly spaced conductive areas 14 which are flat and disc-shaped in size and molded into the molded pad 12 so that the exposed surfaces of each of these conductive areas 14 are generally coplanar with the working surface 28.

Also molded into the molded pad 12 at manufacture is a resistive heating member shown generally in phantom at 18 in FIG. 1. One of the resistive heating elements 18a is shown in FIG. 2, the entire resistive heating member 18 generally coextensive with the array of conductive areas 14 as shown in phantom in FIG. 1.

The resistive heating member 18 is electrically interconnected to wire lead 20 which is connectable to a nine-volt d.c. storage battery 22 for providing a low voltage, low current power supply for producing heat by the resistive heating element 18a. Likewise, the conductive areas 14 are electrically interconnected with electric lead 24 which is interconnectable with a source of pulsed voltage 26 to deliver pulsed electrical signals to each of the conductive areas 14. For convenience and portability, both of these electric power sources may be combined into one housing.

Figure 2:
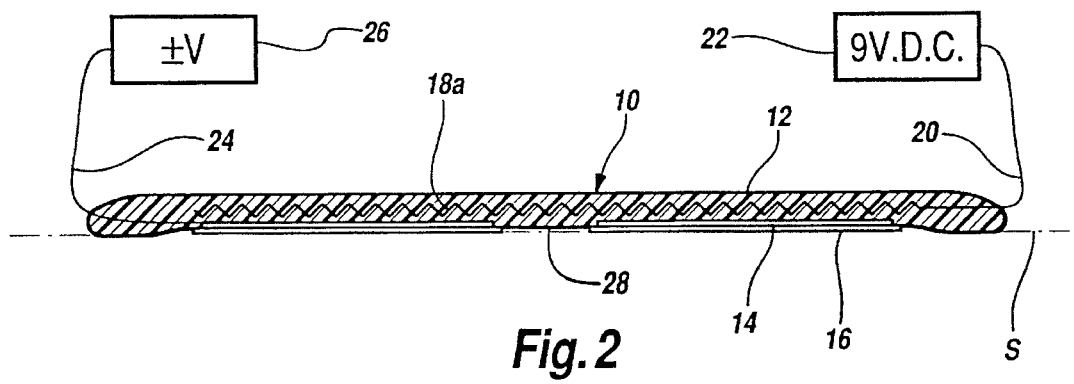
FIG. 2 is a section view of FIG. 1.

The molded pad 12 is thin in nature and manufactured of sufficiently flexible plastic material so as to be formable into a position over any desired body skin area shown in phantom at S in FIG. 2. Prior to applying the pad 12 against the skin S, an array of double-sided adhesive electrodes 16 in FIG. 2 are attached to the skin in the region of soft body tissue to be therapeutic treated by the device 10. These adhesive electrodes 16 are attached to the skin S in an array or arrangement matching the array or arrangement of conductive areas 14 of pad 12. Thus, the double-sided electrodes 16 not only serve to transfer the pulsed electrical impulses received from pulsed voltage source 26 via the conductive areas 14, but also serve to support the entire device 10 atop the skin without the need for straps or other retaining means.

By this arrangement, the molded pad 12 may be easily adhesively attached by interconnection of the exposed surfaces of the conductive areas 14 against aligned double-sided adhesive electrodes 16 which have previously been attached to the skin S. When so installed, simultaneous delivery of pulsed electrical signals and heat into the soft body tissue below the desired skin area S are provided, although each therapeutic function may also be administered separately.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A combination soft body tissue stimulator and heating device comprising:
    a thin, flat flexible molded pad having one side thereof defining a working surface;
    said molded pad including a plurality of integrally molded separate electrically conductive areas each having an exposed conductive surface generally coplanar with said working surface for providing an only means for adhesive attachment of said molded pad to, and for transferring electrical current through a thin disposable double-sided adhesive electrode to a skin area over the soft body tissue against which said adhesive electrode is adapted to be attached;
    resistive heating means embedded in said molded pad spaced from said plurality of electrically conductive areas for heating an area of said molded pad generally coextensive with said plurality of electrically conductive areas;
    means for electrically connecting said plurality of electrically conductive areas to a source of pulsed electrical current for stimulating the soft body tissue;
    means for electrically connecting said resistive heating means to a source of electric power for producing heat.

2. A combination soft body tissue stimulator and heating device comprising;
    a flexible molded pad having one side thereof defining a working surface and having a plurality of separate electrically conductive areas integrally molded with said molded pad and each having an exposed conductive surface generally coplanar with said working surface;
    a plurality of thin disposable double-sided adhesive electrodes each adhesively attachable onto a skin area over the soft tissue in an array which substantially aligns with said conductive areas, wherein adhesive attachment between said conductive areas and said electrodes provides an only means for attachment of said molded pad to the skin areas and further provides means for transferring electrical current through said electrodes to said skin areas;
    resistive heating means embedded in said molded pad electrically isolated from said conductive areas for heating an area of said molded pad which is generally coextensive with said conductive areas;
    means for electrically connecting said conductive areas to a source of pulsed electrical current for stimulating the soft body tissue;
    means for electrically connecting said resistive heating means to a source of electric power for heating the soft body tissue.

3. A combination soft body tissue stimulator and heating device comprising:
    flat flexible molded pad means having one side thereof defining a working surface for supporting integrally molded separate electrically conductive means each having an exposed conductive surface generally coplanar with said working surface, said electrically conductive means for providing an only means for adhesive attachment of said molded pad means to, and for transferring electrical current through, a thin disposable double-sided adhesive electrode to a skin area over the soft body tissue onto which said adhesive electrode is adapted to be attached;
    resistive heating means embedded in said molded pad means electrically isolated from said electrically conductive means for heating the soft body tissue;
    means for connecting said electrically conductive means to a source of pulsed electrical current for stimulating the soft body tissue;
    means for connecting said resistive heating means to a source of electric power for heating the soft body tissue.

* * * * *